(12) United States Patent
Henneberg (10) Patent No.: US 11,169,135 B2
(45) Date of Patent: Nov. 9, 2021

(54) SYSTEM, SENSOR UNIT AND METHOD FOR MONITORING AND EVALUATION OF LIQUID CONDITION

(71) Applicant: C.C. Jensen A/S, Svendborg (DK)

(72) Inventor: Morten Henneberg, Aarup (DK)

(73) Assignee: C.C. Jensen A/S, Svendborg (DK)

( * ) Notice: Subject to any disclaimer, the term of this patent is extended or adjusted under 35 U.S.C. 154(b) by 450 days.

(21) Appl. No.: 16/078,501

(22) PCT Filed: Feb. 23, 2017

(86) PCT No.: PCT/EP2017/054165
§ 371 (c)(1),
(2) Date: Aug. 21, 2018

(87) PCT Pub. No.: WO2017/144588
PCT Pub. Date: Aug. 31, 2017

(65) Prior Publication Data
US 2019/0101520 A1 Apr. 4, 2019

(30) Foreign Application Priority Data
Feb. 23, 2016 (EP) ..................................... 16156933

(51) Int. Cl.
*G01N 33/28* (2006.01)
*F01M 1/10* (2006.01)
(Continued)

(52) U.S. Cl.
CPC ........... *G01N 33/2888* (2013.01); *F01M 1/10* (2013.01); *F01M 11/10* (2013.01); *F16N 29/00* (2013.01);
(Continued)

(58) Field of Classification Search
CPC ......... G01N 33/2888; G01N 35/00871; F01M 1/10; F01M 11/10; F01M 2011/146;
(Continued)

(56) References Cited

U.S. PATENT DOCUMENTS 3,526,127 A 9/1970 Sarkis
5,646,341 A 7/1997 Schricker et al.
(Continued)

FOREIGN PATENT DOCUMENTS

EP 2530367 A1 12/2012
EP 2749853 A2 7/2014

OTHER PUBLICATIONS

PCT/EP/2017/054166; International Filing Date Feb. 23, 2017; ISA Written Opinion dated Jun. 14, 2017; C. C. Jensen A/S (5 pages).
(Continued)

*Primary Examiner* — Suman K Nath
(74) *Attorney, Agent, or Firm* — Barclay Damon LLP (57) ABSTRACT

The present disclosure relates to a sensing unit and method for monitoring the condition of a liquid, the sensing unit comprising at least one sensor and an evaluation unit. The sensing unit is adapted to measure two or more physical parameters of the liquid by use of at least one sensor, where the parameters relate to at least liquid degradation or wear debris particle generation. The at least one sensor is adapted to provide at least two signals, each signal providing its values in a fashion suitable for developing a mean value and a non-zero variance or a variance different from zero over a course of at least two measurements. The evaluation unit is adapted to correlate the measured signals, and to evaluate the condition of the liquid by comparing the measured at least two parameters. Thereby, a reliable monitoring system giving continual feedback on the performance of the lubricant and the machine in an auto-correlated manner is obtained, thus allowing continual adjustments to improve uptime and machine life.

20 Claims, 6 Drawing Sheets

(51) Int. Cl.
  *F01M 11/10* (2006.01)
  *F16N 29/00* (2006.01)
  *G01N 35/00* (2006.01)

(52) U.S. Cl.
  CPC . *G01N 35/00871* (2013.01); *F01M 2011/146* (2013.01); *F16N 2250/04* (2013.01); *F16N 2250/08* (2013.01); *F16N 2270/56* (2013.01); *F16N 2270/60* (2013.01)

(58) Field of Classification Search
  CPC .. F16N 29/00; F16N 2270/56; F16N 2270/60; F16N 2250/04; F16N 2250/08
  See application file for complete search history.

(56) References Cited

U.S. PATENT DOCUMENTS

| | | | |
|---|---|---|---|
| 6,324,899 | B1 | 12/2001 | Discenzo |
| 6,449,580 | B1 | 9/2002 | Bardetsky et al. |
| 7,581,434 | B1 | 9/2009 | Discenzo et al. |
| 2004/0128059 | A1 | 7/2004 | Kunz et al. |
| 2005/0066711 | A1* | 3/2005 | Discenzo ........... G01N 33/2888 73/64.56 |
| 2012/0046896 | A1 | 2/2012 | Flandrois et al. |
| 2014/0130587 | A1 | 5/2014 | Von Herzen et al. |

OTHER PUBLICATIONS

PCT/EP2017/054165; International Filing Date Feb. 23, 2017; ISA Written Opinion dated Mar. 24, 2017; C. C. Jensen A/S (7 pages).
Nov. 21, 2018 PCT/EP/2017/054166; International Filing Date Feb. 23, 2017; International Preliminary Report of Patentability May 17, 2017; C. C. Jensen A/S (13 pages).
PCT/EP/2017/054165; International Filing Date Feb. 23, 2017; International Preliminary Report of Patentability Jul. 2, 2017; C. C. Jensen A/S (13 pages).
U.S. Appl. No. 16/078,814, filed Aug. 22, 2018, nationalization of International Application No. PCT/EP2017/054166.

* cited by examiner

SYSTEM, SENSOR UNIT AND METHOD FOR MONITORING AND EVALUATION OF LIQUID CONDITION

CROSS-REFERENCE TO RELATED APPLICATIONS

This application is a national stage application pursuant to 35 U.S.C. § 371 of International Application No. PCT/EP2017/054165, filed on Feb. 23, 2017, which claims priority to, and the benefit of, European Patent Application No. 16156933.0, filed on Feb. 23, 2016. The entire contents of such applications are hereby incorporated by reference.

FIELD OF THE INVENTION

The present invention relates to a system and a sensing unit for monitoring and evaluating the condition of a liquid and a method of monitoring the condition of a liquid.

BACKGROUND

Machinery applied for multiple purposes in on-shore and off-shore industries, such as mining industry, power generation industry, wind turbine industry and aboard ships, should operate efficiently for extended periods of time, ideally only stopping when there is no need for their function. In reality, machines stop abruptly and in a planned fashion for a variety of other reasons. A major cause of downtime is due to breakdowns caused by wear on the machine and furthermore planned maintenance to avoid this wear.

The parts of the machine most exposed to wear are the moving parts, where lubrication is applied to increase efficiency and to avoid metal-on-metal wear. The lubricant absorbs worn off particles and carries them downstream, where a filtration unit, typically an in-line hydraulic filter, absorbs the largest particles and reintroduces the rest to the machinery anew. When excessive particles are reintroduced into the machinery, they abrade the moving parts which both decreases operating efficiency and produces yet more and larger wear debris thus further speeding up the gear degradation exponentially as large particles tear off yet larger particles. This also clogs the filter.

The lubricating liquid is most often an oil with additives. These additives are introduced to improve different functions of the oil, such as increasing viscosity for elevated temperature operation to counter chemical breakdown or for lubricity. Over time, the oil and/or additives break down, thus acidifying the oil. If left alone, the acidified oil then corrodes the machine parts which it comes into contact with. Said machine parts then need to be changed resulting in costly repairs, loss of productivity for the machine and if the machine was part of a large operation such as a ship, the functioning of this overall system being impaired. Such a breakdown may then be disastrously expensive.

Furthermore, the relationship between wear debris particle generation and liquid degradation, though unclear in its exact nature, includes at least a two-way positive feedback loop, where an increased wear debris generation wears the oil, and a worn oil corrodes the machine thus generating wear debris particles. This further problematises both of these issues when they arise as especially large particle wear debris generation has an exponential growth and has to be stopped immediately on identification.

Ideally, when the liquid comprises too many wear debris particles and/or the liquid is degraded past a certain point, the machine stops and a maintenance crew can correct the issue by for example cleaning the machine and reapplying a new liquid or changing the in-line filter. Because such machines are closed systems, correctly assessing when to open up the machine for inspection and/or maintenance is of great interest.

To avoid any untimely breakdown with accompanying excessive machine wear, machines are typically scheduled for maintenance or oil analysis on a regular basis. For example, at a set of predefined dates, the machine is turned off, and a maintenance crew opens the system taking a sample of the oil for off-site evaluation and/or cleaning the system according to some predefined maintenance procedures. U.S. Pat. No. 3,526,127 A discloses a method and apparatus for automatically testing oil condition assisted by computer help and reporting the results thereof. Unfortunately, this is performed off-site and is an expensive method for several reasons. Opening the system may introduce foreign elements into the closed system, and the act of opening a hatch may release particles from the inside thus interrupting the flow and causing down-time later. These proactive maintenance procedures are defined from a lowest common denominator among all machines of the type thus adding a safety factor to this. Though it makes sense as breakdowns are more costly than planned maintenance, any unnecessary downtime is very expensive, especially when this downtime furthermore introduces a risk of subsequent breakdown or requires the large operation, such as a ship, to stop its operation.

Furthermore, not all machines are worn the same. The operating style of its crew is very important to the potential uptime and machine life of a machine. For example, a machine, which is alternately turned off and on at maximal speed, will wear significantly faster than a machine operating within its optimal operating ranges. Then, the better performing machine has more maintenance downtime than actually needed, while a poorly managed machine may not be identified as being poorly managed until the machine has been damaged which may leave the exact culprits of this mismanagement hard or impossible to pinpoint.

To avoid critical damage to the equipment, sensors may be introduced to monitor the liquid for accumulation of wear debris particles as well as liquid degradation. However, the hydraulics of the system have to function perfectly at all times to get a representative image of wear debris particles in the liquid which is difficult to attain. In the art, wear debris particles are typically monitored with optical sensors, while liquid degradation is measured by electrical impedance spectroscopy type sensors.

U.S. Pat. No. 6,449,580 B1 discloses testing the permittivity of a working fluid over a range of temperatures thus identifying the temperature where the permittivity is the most sensitive to changes in temperature. This allows estimation of viscosity, acid content, moisture content and working fluid density by measuring over a test period nothing but permittivity and temperature. This assumes that relationships among all parameters stays fixed for the lifetime of the system.

EP 2749853 A2 describes a sensor integrated into an oil drain for an oil system such as a reciprocating engine for a motorized vehicle. The sensor measures various individual aspects of the oil condition.

Raw sensor signals will fluctuate significantly between readings for several reasons, one being system fluctuations, another being noise due to the sensor. To compensate for this, sensors are built and sold with integrated averaging capabilities that increase sensor precision thus allowing an understanding of the system and liquid condition being more general and representative.

Furthermore, the sensor technologies of the art have several distinct weaknesses. For example, certain important particle sensor types cannot differentiate between water particles and/or entrained air bubbles and wear particles, whose readings may suddenly spike thus causing an immediate and unneeded system stop.

SUMMARY OF THE INVENTION

It is therefore an object of this invention to solve the above-mentioned problems. In accordance with the invention, there is provided a sensing unit for monitoring the condition of a liquid. The sensing unit comprises at least one sensor interface and an evaluation unit, where the sensor interface is adapted to measure two or more raw signals, each raw signal corresponding to a parameter of the liquid where said parameters relate to at least liquid degradation or wear debris particle generation. The sensor interface is further adapted to transmit at least two transmission signals to said evaluation unit, each transmission signal corresponding to a raw signal, characterised by each transmission signal having a variance comparable to the variance of its corresponding raw signal, and the evaluation unit being adapted to evaluate the condition of the liquid by inter-correlating the measured at least two parameters.

Thereby, an improved sensor system is provided.

Sensors of the art are adapted to average readings prior to transmittal to reduce signal noise. This allows the maintenance crew to diagnose the liquid system condition since outputted values are steady, and changes thereto constitute some sort of disruption. This increases sensor precision at the expense of signal variance which is traditionally accepted as variance is considered signal noise. In the present invention, this variance constitutes a second instrumental data source, and signal noise and imprecision are accepted. By using sensors that do not pre-process the data it measures before passing it on to the evaluation unit, the evaluation unit is surprisingly enabled to perform genuine statistical data analysis on the liquid system.

By combining this improved data fidelity and variance with inter-correlating at least two parameter measurements, genuine and system-, and context-specific liquid condition prognosis is achievable in accordance with the invention.

Thereby, accurate and precise diagnostication of system disruptions as well as identification of system behaviour drifts and trajectories is obtainable. In other words, if the readings of a conventional system varies, the maintenance crew knows something has changed; but not what or why. By performing raw sensor data transmission, statistical analysis and inter-correlating the signals, much more information about the actual state of the system is achievable. Minor operating pattern changes become noticeable, and a maintenance crew may act instantly instead of having to wait until the operating parameters have crept past some arbitrary sensor hardware-dependent inertia threshold.

The sensor interface is adapted to measure the condition of the liquid, and provide these measurements for the evaluation unit. By providing a series of measurements, signals are provided to the evaluation unit being consecutive measurements.

By the variance being comparable is meant that the variance of the transmission signal is significantly like the variance of the raw signal, such as essentially no measurement information being filtered from the raw signal by the sensor before transmission. It may further have a comparable mean value and hence distribution.

In an embodiment, the sensor interface does not pre-process the raw signals before passing them on as transmission signals. Thereby, unfiltered signals are provided to the evaluation unit.

In an embodiment, each transmission signal corresponds to a raw signal. In an embodiment, each transmission signal corresponds substantially to a raw signal. In an embodiment, for each raw signal provided by the sensor interface, a transmission signal is transmitted to the evaluation unit.

In an embodiment, each transmission signal resembles a corresponding raw signal. By resembling is meant that the information contained in a transmission signal is equal to the information contained in a corresponding raw signal, meaning that any data handling performed by the sensor interface is applied proportionally to all the raw data points in the raw signal thus producing a transmission signal with a data variance and distribution of data points proportional to the raw signal from which it is produced.

In an embodiment, for each transmission signal transmitted from the sensor interface to the evaluation unit, the sensor interface has sensed at most one raw signal, at most two raw signals, at most three raw signals, at most four raw signals, at most five raw signals, at most six raw signals, at most seven raw signals, at most eight raw signals, at most nine raw signals, or at most ten raw signals to produce the transmission signal.

In an embodiment, the variance of transmission signals is not substantially lower than the variance of the raw signals.

In an embodiment, the transmission signal has a variance similar to the variance of the raw signal. By similar to is meant that the sensor interface is allowed to correct the data by removing outlier raw data points being part of a raw signal to produce the transmission signal. In an embodiment hereof, such outlier signals may be removed for any number of raw data points. In another embodiment hereof, such outlier data points may be removed for every three, four, five, six, seven, eight, nine, ten, fifteen, twenty, twenty-five, thirty, thirty-five, forty, forty-five, fifty, fifty-five, sixty, sixty-five, seventy, seventy-five, eighty, eighty-five, ninety, ninety-five or a hundred raw data points.

In an embodiment, one or two such outlier data points may be removed to produce said transmission signal. In another embodiment, 1%, 2%, 3%, 4%, 5%, 6%, 7%, 8%, 9% or even 10% of said raw data points may be removed to produce said transmission signal.

In a preferred embodiment, the transmission signal has a variance equal to the variance of the raw signal. By equal is meant that no data correction is performed by the sensor interface.

In an embodiment, at least one parameter is correlated with reference data. In another embodiment, at least two parameters are correlated with reference data. In a further embodiment, the reference data comprise historical data of the parameter in question for the given system which allows a trend analysis that informs of system wear or out-of-balance operations. In a further embodiment, the reference data comprise predetermined, expected values for the system based on either factory tests or a at least one other system having been or being in operation. In a further preferred embodiment, the reference data comprise a run-in period of the current system.

The condition of a liquid may be understood as the state of the liquid in terms of the presence of wear debris particles in the liquid and in terms of the degree of chemical degradation of the liquid compared to a freshly provided virgin liquid in terms of breakdown of the liquid and/or any additives in it, typically acidifying the liquid.

The evaluation unit is adapted to correlate the measured parameters. By correlating the parameters is meant that their mutual and/or reciprocal relationships are established. This may be performed in any degree of precision and by any convenient method.

The correlation may pertain to relationships between static sensor readings. For example, the effect of high wear debris measurements on liquid degradation measurements is assessed, or in other words, the likelihood of specific parameter readings in one of the parameter readings given a specific value in another. Correlation may relate to relationships between trajectories within parameter readings, such as the effect of an increase in one parameter value on the expected value of another. Further, correlations may relate to a combination of static sensor readings and trajectory sensor readings.

Correlations are at least one-way relationships, and in a preferred embodiment, correlations are two-way relationships among all relevant parameters meaning that the cause-effect relationships are assessed reciprocally.

In one embodiment, more complicated relationships may be assessed through these correlations such as the effect on a third parameter by the states and/or trajectories of a first and second parameter in conjunction. For example, temperature may not be affected by either liquid degradation or wear debris particles, except when both are within certain ranges, such as both being high.

In one embodiment, correlations are carried out on parameters in the mathematical sense, where the inter-dependence of parameter states or trajectories is determined, for example with statistical modelling using Hotelling $T^2$ models.

The correlation may be carried out continuously or at a predetermined frequency. Continuous correlation and condition monitoring may be an advantage so that any liquid degradation and/or change in wear debris particle generation may be detected and acted upon before the equipment is damaged. However, the evaluation may also be adapted to correlate the measured parameters in intervals of seconds, minutes or even several hours. The measured parameters may then be stored and/or transferred to e.g. a database or server either on-site of off-site relative to the liquid system.

The evaluation of the condition of the liquid by correlating the measured parameters may be carried out at a pre-defined rate. Thus, the monitoring and evaluation may be carried out regularly, e.g. every second, minute, hour, day or after any convenient period of time. Through the correlation, specific combinations of signals are known to produce associated operating conditions. In one embodiment of the invention, this allows sophisticated and high fidelity feedback to users concerning the current state and expected future operating states.

Through a first operating phase, a table of operating patterns may be developed which can be used for assessment of wear and/or errors in the system which can then be managed in time to prevent excessive wear, false alerts and breakdowns.

By measuring at least one of the liquid degradation or particle wear generation in a fashion, which allows a mean value and a variance different from zero and correlating these signals, the sensing unit allows significantly more precise operation monitoring. For example, a spike in one parameter measurement may be disregarded as being a false reading if data from another parameter signal shows this. For example, while a particle sensor may see a spike in particle generation and may normally alert to excessive wear debris in the system, this may be disregarded when compared with other parameters such as water content in the liquid. Some particle sensors cannot differentiate between water and wear debris particles, and so a spike in particle count may under certain circumstances be ignored, for example when water content also spikes since some liquid lubrication systems may comprise more water than wear debris before an alert is needed. As an example, this allows the maintenance crew not to intervene on false alerts, but instead warns them of the more sophisticated scenario present.

Having a reliable monitoring system giving continual feedback on the performance of the lubricant and the machine in an auto-correlated manner furthermore means that the maintenance and operating crew know that the equipment is being monitored and that data is readily available on its actual performance thus allowing continual adjustments to improve uptime and machine life.

Significantly, having a continual detailed reading on wear particles and/or liquid degradation allows continual assessment of the state of the equipment which allows reliable machine life projections and allows avoiding taking the machine out of operation for scheduled maintenance if it does not need it. This is naturally of great financial interest especially if the machine is part of a system which will also have to be taken out of operation in such a situation, such as a ship which would have to go into dock.

In one embodiment of the invention, the sensing unit is adapted to measure liquid degradation. Within the present invention, degradation of the liquid may be understood as comprising for example degradation caused by oxidation and loss of additives. In an embodiment of the invention, it is measured by electrical impedance spectroscopy (EIS) type sensors.

By measuring liquid degradation, the maintenance crew is informed of changes to the chemical composition of the liquid which helps them ascertain the need for changing the liquid as well as the expected particle wear generation.

In one embodiment, at least one liquid degradation sensor interface is placed downstream from an off-line filter. By placing the liquid degradation sensing interface downstream, the liquid comprises fewer wear particles during monitoring, whose presence would impair EIS readings.

In one embodiment of the invention, the sensing unit is adapted to measure wear debris particle generation. Within the present invention, wear debris particles may be understood as being caused typically by metal-to-metal contact, for example because of excessive wear, contamination, improper lubrication, a change in operating conditions, and/or other factors. Sensors for measuring wear debris particles may be based on e.g. measuring said particles optically and/or inductively. Typically, the former has a higher sensitivity to smaller particles than the latter which is, however, able to distinguish particles based on material.

By measuring wear debris particle generation, the abrasiveness of the liquid can be ascertained as well as the generation of new wear particles which describes system and machine erosion.

In one embodiment, at least one wear debris particle sensor interface is placed upstream from an off-line filter. Because the off-line filter typically has its inlet at the bottom of a liquid reservoir, whose content is substantially dormant, the inlet liquid is typically contaminated to a higher degree than the liquid of most other locations of the system because the contaminants sediment here. Placing the wear debris particle sensor interface upstream then allows sensing substantially one of the most contaminated gradients of the liquid thus rapidly describing liquid condition of changed wear debris generation.

Correlating the at least two signals is achieved by running the system in an initial operational phase which establishes a baseline of the compounded operating patterns of the at least two signals. For example, over the course of a month, wear debris particles and relative humidity in an oil-based lubricant are measured to ascertain an operating baseline. This establishes a mean value, a variation different from zero as well as accepted and unaccepted operating patterns for the combined values of the two sensor interfaces.

For example, if relative humidity is high, and small particle count is high, then particle count is caused by the water content, and at least a part of the high particle count can be ignored if the system behaves controllably otherwise. Or if, due to the higher sensitivity of the sensors, a slight increase in wear debris particles absent of a correlated increase in relative humidity is observed, the system gives an alert well before a conventional system would be able to react to this change.

In one embodiment of the invention, the parameters further relate to a pressure, a temperature, and/or a water content of the liquid. By measuring these additional parameters, the precision of the measurement of the liquid condition is improved. Furthermore, the precision of the individual measurements is also improved by further correlations with each added parameter. For example, a sensing unit measuring wear particles and liquid degradation improved by measuring temperature will allow accounting for changed resistance and conductance of the liquid on account of temperature thus improving liquid degradation monitoring.

This allows yet more precise liquid condition monitoring and with this improved operating control.

In one embodiment of the invention, the sensing unit is adapted to measure three parameters related to liquid degradation, two parameters related to wear debris particle generation, two parameters related to pressure of the liquid, and one parameter related to the temperature of the liquid by use of the at least one sensor.

This allows a differentiated understanding of the condition of the liquid as well as the most precise understanding of each of the individual parameters because of the correlations performed by the evaluation unit. Any sensor interfaces useful for describing the liquid and/or system condition is useful for the invention. Conveniently, the sensing unit may comprise any of the following sensor interfaces:

an electro impedance spectroscopy type sensor for liquid degradation,
relative humidity sensor for water content measurement,
an optical sensor for small wear debris particles,
a ferromagnetic/inductive type sensor for large wear debris particles,
a pressure sensor
a viscosity sensor
an acoustic/opto-acoustic sensor
an imaging sensor
and a temperature sensor.

In an embodiment, the parameters can further relate to consumed power, electrical current, liquid flow and/or machine on/off signals. These input are useful in combination with other sensor signals to diagnose certain system conditions. Knowing for example that the power need increases, while the flow remains constant, may indicate a narrowing of a channel somewhere in the system, while the operating mode may for example describe expected temperature or wear debris particle generation.

In an embodiment of the invention, the sensing unit is embedded in a system for monitoring the condition of a liquid, the system comprising a system inlet for receiving an inlet flow of contaminated liquid, a system outlet for releasing an outlet flow of filtered liquid, a filtration unit, which is in fluid communication with the system inlet and the system outlet, the filtration unit comprising a filter, which is adapted to receive the contaminated liquid and to release the filtered liquid, and the aforementioned sensing unit.

Providing a sensing unit in a system for filtering a liquid allows the data provided by the sensing unit to be compared with data correlated with other equipment/installations which also comprise a system for filtering a liquid and including similar elements, either as part of the same closed liquid system or preferably in other similar systems.

In all, this provides a solid identification and evaluation of how the data regarding inter alia liquid degradation and wear debris particle generation develops ideally, i.e. the operating patterns and overall expected development, for a situation in which the liquid is filtered ideally, for example without any errors in the equipment or leakages in the system. Thus, identification of such a pattern and/or development can be used for qualitative evaluation with the purpose of estimating the remaining life-time of the equipment and also estimating possible future events that could later lead to damage/severe wear on the system.

Furthermore, providing a sensing unit at a centralised location in a system for filtering a liquid with predetermined elements, which may be used and compared with systems at other locations, allows both the best location for the specific measurements as well as correlating the data for later use. For example, this allows optimum liquid flow rate measurements and electrical impedance measurements.

Thereby, optimum parameters and parameter values may be used for correlating the data compared to uncoordinated stand-alone sensor-installations.

In an embodiment, the filtering system is arranged aboard a ship. The filtering system may be an oil filtration system connected to an engine or a machine aboard a ship. The engine or machine aboard a ship may be related to a crane, stern thruster or an azimuth thruster, or it may be connected to systems related to the propulsion machinery.

In another embodiment, the filtering system is arranged in a wind turbine. The filtering system may be an oil filtering system connected to the gear box system or to the hydraulic pitch control system.

In a third embodiment, the filtering system is applied in power generation plants. The filter system may be connected to the power turbine lubricating and control oil system.

The system inlet may draw liquid from any point in the system, typically from either the top or bottom of a reservoir placed downstream from the machine, where the liquid at the bottom is relatively at rest and comparably more contaminated than the liquid at the top. The outlet may release the filtered liquid anywhere in the system, for example directly to the machine. In a preferred embodiment, it releases the filtered liquid at the top of the mentioned reservoir.

The filtration unit can be any type and kind performing a separation of contaminants from the liquid relative to a virgin liquid, for example removing solids such as wear debris particles or removing fluids such as water or air. The filtration unit can take any place which is in fluid communication with the system, such as an in-line hydraulics filter. In a preferred embodiment, the filter for handling the liquid may be an offline fine filter and may as such be a depth fine filter, such as a CJC™ HUD 27/27 Fine Filter Unit.

In an embodiment, wear particles are preferably monitored upstream from the filtration unit to supply a reading on the machine wear which would be at least partially negated by placing the sensor after a filtration unit especially as pertains to large particles.

In an embodiment of the invention, liquid degradation is monitored downstream from the filtration device to negate most of the noise produced in EIS readings by magnetic particles, such as wear debris particles.

In an embodiment of the invention, the liquid refers to an oil product and the filtration unit of the aforementioned system is an oil filter. In this embodiment, the liquid is predominantly oil, although additives may be used to enhance certain desired features of the oil, such as viscosity or lifetime. Oil may conveniently be used as lubrication as this is an effective lubricant and reduces machine wear significantly.

In an embodiment of the invention, wherein the liquid is an oil product, the viscosity of the oil product is between 1 and 5,000 cSt.

In an embodiment of the invention, wherein the liquid is an oil product, the operating temperature of the oil is between 0 and 120° C.

In an embodiment of the invention, it pertains to a method of monitoring the condition of a liquid. The method comprises three steps. Firstly, a sensing unit is provided for monitoring the condition of the liquid, the sensing unit comprising at least one sensor and an evaluation unit, measuring two or more parameters of the liquid by use of the at least one sensor, where the parameters relate to at least liquid degradation or wear debris particle generation, and the at least one sensor provides for each signal a mean value and a variance different from zero over a course of at least two measurements. Secondly, the measured at least two parameters are correlated. Thirdly, the condition of the liquid is evaluated based on the measurement correlation.

In an embodiment of the invention, the evaluation of the condition of the liquid further comprises comparing the measured and/or correlated parameters to reference data. This reference data may take any convenient form and in one embodiment, it comprises at least baseline data and/or inter-system data.

Baseline data is generated over the course of an initial operational phase of the system in which the sensing unit is used. Preferably, it takes the form of operational patterns with historically identified, contextual consequences. For example, a change in water content may normally signify for example leakage but may have been found to adjust itself within an acceptable range for a certain, possibly old system. Acceptable and unacceptable operational patterns are identified and defined allowing quick feedback on measurement creep thus leading to out-of-balance operations as well as uniquely acceptable operational conditions, where conventional, uncoordinated or even coordinated but uncorrelated sensor signals would give false alarms from the same sensor measurements. Inter-system data is a collection of at least one set of baseline data collected from a system whose run-in period was prior to installation of the one, wherein the current sensing unit is placed. In a preferred embodiment, inter-system data comprises a wide range of such previous sets of baseline data and furthermore comprises data sets for the entire machine life of some of these previous data sets, preferably at least one.

In one embodiment of the invention, the baseline data for the current system is updated continuously throughout the lifetime of the system. This allows the system to adapt to its own changing wear over time thus allowing better operational diagnosing, especially when correlated with inter-system data. Significantly, this allows the system to lower the thresholds for alerts as machine wear makes it more vulnerable to divergences from optimal operational patterns. For example, as a machine gets older, it may develop a tendency to overheat which means that early alerts if it was building heat would be of great interest. This increased parameter sensitivity would express itself as larger variances for the measured parameter thus resulting in flatter normal distributions, possibly even with fat tail distribution, meaning that supposedly very unlikely events, such as system breakdown, are significantly more likely than anticipated through statistical analysis. Additionally, system wear may express itself in the form of a creeping mean value for a given parameter, such as a liquid system getting hotter with age.

Furthermore, this embodiment of the invention allows the evaluation unit to develop sophisticated evaluations of the changing sensitivities of the system, alerting for example to the exemplified creep in heat build-up or a higher operating temperature. This expresses itself simply as the change in any parameter variance. In one embodiment of the invention, unexpected changes in variances or mean values prompt a warning signaling possible long-term wear on the machine.

In an embodiment of the invention the evaluation of the condition of the liquid is carried out continuously. By evaluating the condition of the liquid continuously, precise sensor readings are achieved.

In an embodiment of the invention the evaluation unit is adapted to send a signal reflecting the evaluated condition of the liquid. A signal may be sent to any type of receiver, such as an on-site computer or an off-site computer, or it may communicate its signal directly to the maintenance crew. In a preferred embodiment, an off-site computer handles the data analysis and returns the resultant signal to a convenient receiver at the machine site, such as a computer used by the maintenance crew.

DETAINED DESCRIPTION OF THE EMBODIMENTS

Figure 1:
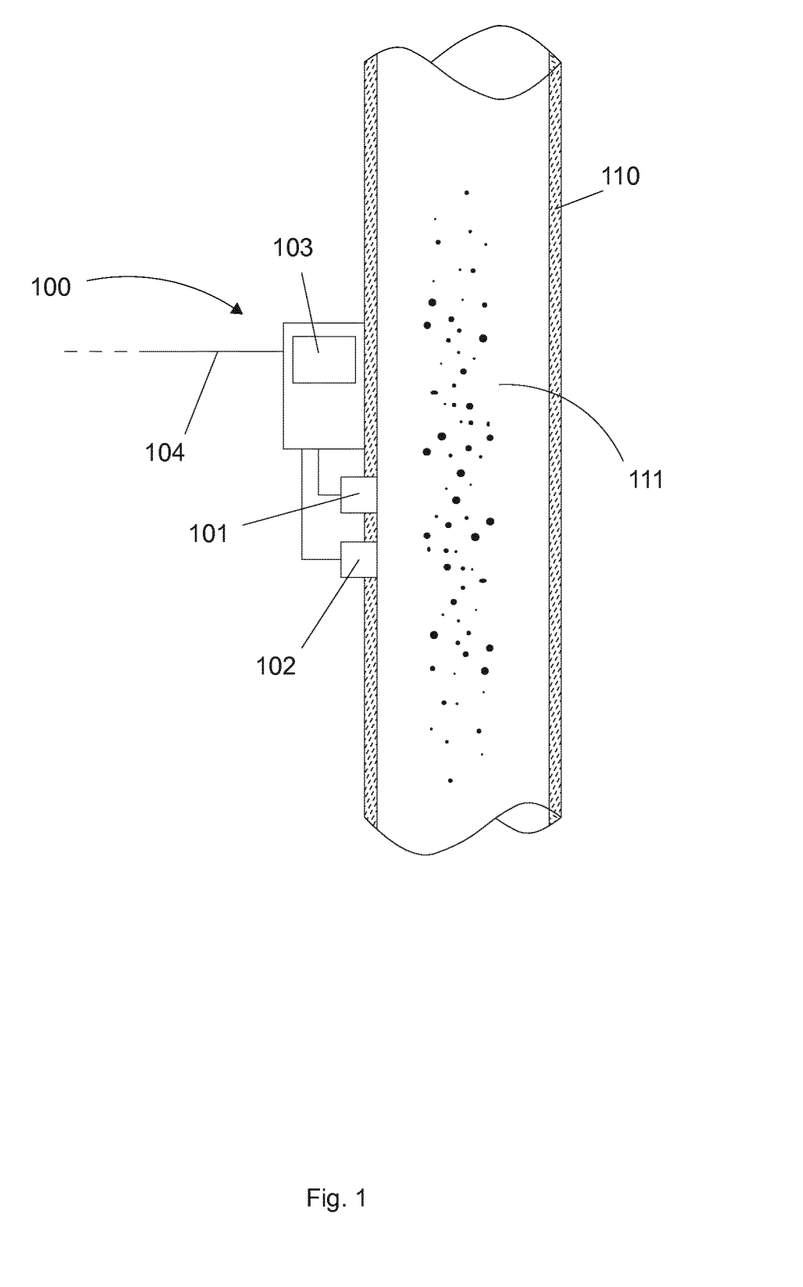
FIG. 1 illustrates a sensing unit according to the present invention measuring wear particle count and liquid wear in a pipe.

FIG. 1 illustrates a sensing unit 100 according to the present invention. The sensing unit is mounted onto a pipe 110 fitted for transporting a liquid 111 in the system. The liquid is illustrated as containing contaminants such as wear debris particles. The sensing unit comprises a first sensor interface 101 and a second sensor interface 102 for receiving measurements on liquid parameters and an evaluation unit 103 to calculate the condition of the liquid from parameters and historical data. Furthermore, the sensing unit is fitted with a transmission unit 104 for sending the measured data to any convenient receiver.

Only the sensor interfaces must be placed in close proximity to the liquid, in whatever manner allows their operation, such as being fitted inside the liquid-filled closed system or preferably near it. The rest of the sensing unit may also be mounted anywhere close to the liquid or even far away from it in any convenient manner. The sensor interfaces may be placed so as to sense the liquid in a reservoir or preferably in a pipe. Internally, the sensing unit must be in electrical communication, but its parts may be dispersed throughout space.

The sensor interfaces must be of types that send their measurements at least significantly unfiltered. For example, some sensors will normalise their measurement values over a number of measurements and only transmit the mean to cancel out noise. These pre-normalisations remove crucial data for subsequent data manipulation of the invention.

Figure 6:
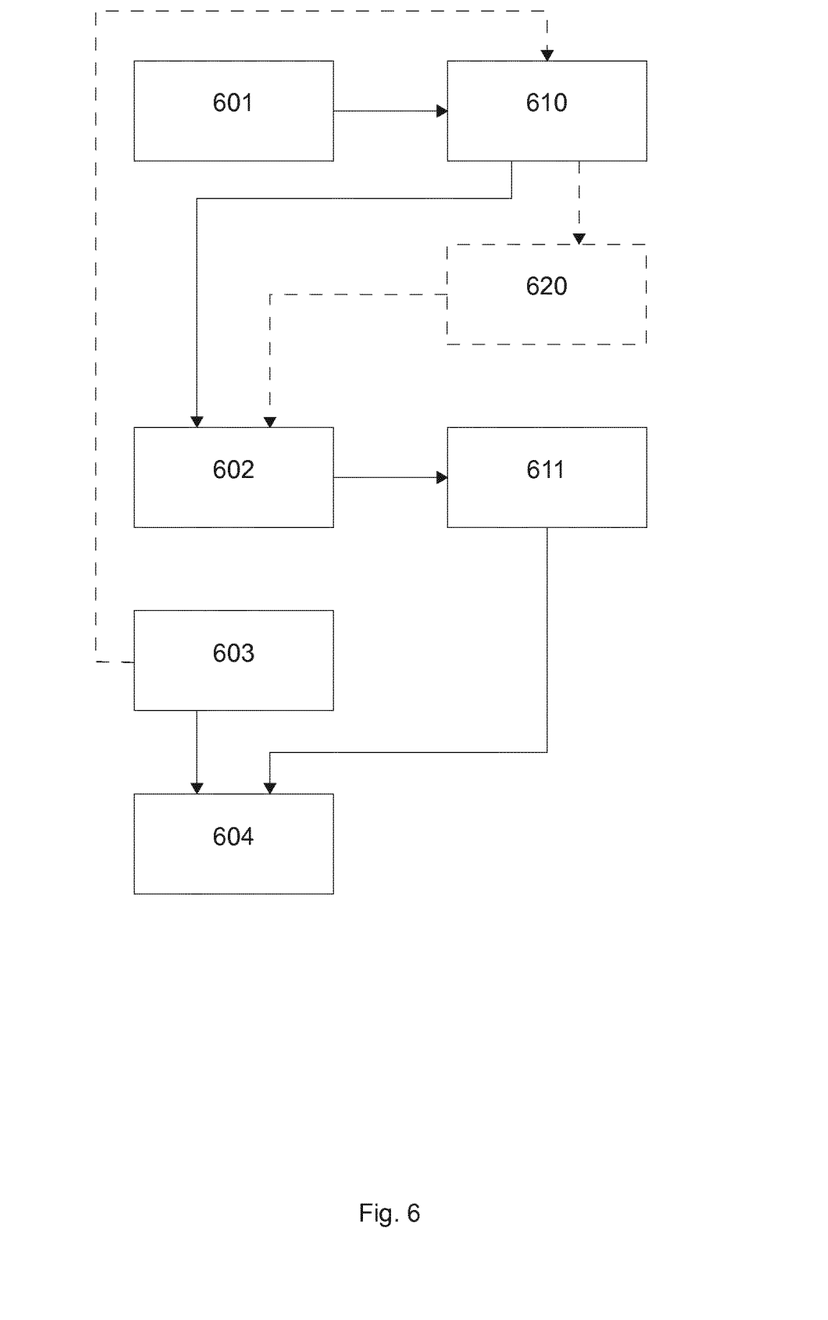
FIG. 6 illustrates a control and data flow according to the present invention.

The evaluation unit is in electrical communication with the sensor interfaces and is fitted to perform correlations among these according to some predefined set of operating patterns (see FIG. 6).

In one embodiment, the evaluation unit 103 is adapted to receive signals through the transmission unit 104 as well as from the first and second sensor interfaces. For example, a signal from through the transmission unit may be updated data on system operation patterns, such a signal constituting a fine-tuning of the operation and control of the evaluation unit. In another embodiment, the evaluation unit is adapted to perform these self-adjustments without outside instructions.

The transmission unit may be a copper wire, a wireless transmission unit, such as one relying on Bluetooth or Wi-Fi, or any convenient signal-bearing unit. In one embodiment, the transmission unit is adapted to send and receive signals in both directions.

The sensing unit is fitted to receive at least two signals relating to the condition of the liquid, one from a first sensor interface 101 and another from a second sensor interface 102. The sensing unit may comprise one or more sensor interfaces as long as two or more measurements are performed among sensor interfaces relating to the condition of the liquid.

Figure 2:
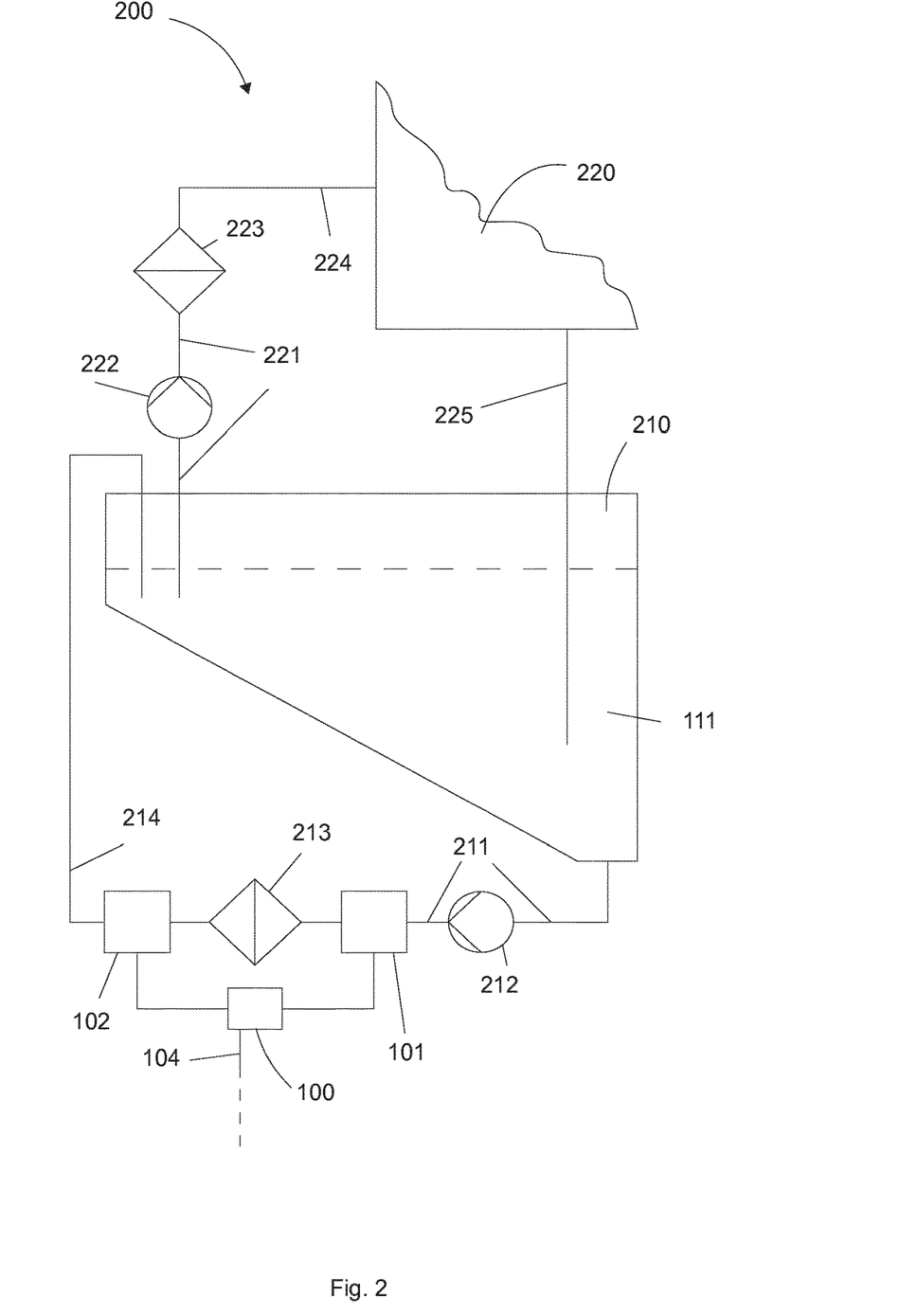
FIG. 2 illustrates a liquid condition monitoring system according to the present invention.

FIG. 2 illustrates a liquid lubrication system 200 for lubricating a machine 220. The system comprises an in-line filter 223 upstream from the machine for removing especially the large particles before they enter the machine, a liquid reservoir 210 for containing liquid substantially at rest, and an off-line filter 213 for purifying the liquid of smaller particles and other contaminants.

The liquid reservoir 210 is placed downstream from the machine 220, and wear debris particles and other contaminants sediment in it thus creating a purity gradient of the liquid in the reservoir, where the uppermost part of the liquid is the purest, and the lowermost part is the most contaminated by for example wear debris particles. This effect is driven by gravity.

The in-line pump 222 draws liquid from the uppermost part of the liquid reservoir, into an in-line inlet pile 221, through an in-line filter 223, where it is filtered for large particles. The purified liquid is inserted into the machine 220, where it is contaminated, and then through an in-line outlet pipe 224. The contaminated liquid is reintroduced in the reservoir, typically close to the bottom.

Conversely, the off-line pump 212 typically draws contaminated liquid from the bottommost part of the liquid reservoir, through an off-line inlet pipe 211, into the off-line filter 213, through an off-line outlet pipe 214 and deposits the purified liquid near the top of the liquid reservoir 210.

The sensing unit may be placed at any convenient position within this system. Most likely, it is placed in conjunction with a filter, such as the in-line filter and/or the off-line filter. In one embodiment, it is placed next to the off-line filter, and in a preferred embodiment, a first sensor interface is placed upstream 211, and a second sensor interface is placed downstream 214 relative to the off-line filter 213.

In another embodiment, two sensor interfaces comprised in the sensing unit are placed upstream and downstream relative to the in-line filter 223, respectively.

The sensor interfaces may be adapted collectively to measure any number of two or more parameters relating to liquid condition, such as wear particle debris, liquid wear, temperature, pressure and water content. Other parameters relating to the overall operation and system may be measured as well, such as power usage.

In one embodiment, wear particle debris is measured optically and conductively, and liquid wear is measured with electrochemical impedance spectroscopy.

In one embodiment, the first sensor interface is adapted to measure at least wear particle debris.

In one embodiment, the second sensor interface is adapted to measure liquid wear.

Figure 3A:
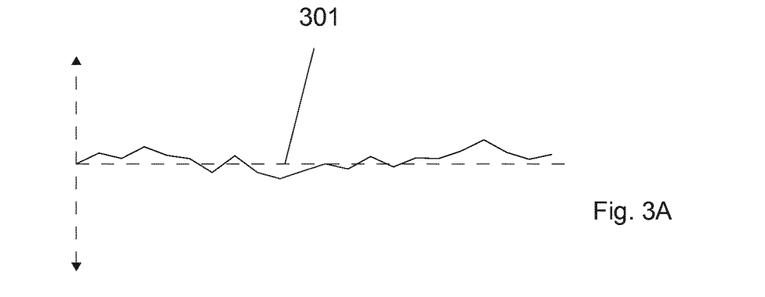
FIG. 3 illustrates three example measurement data sets differentiable with the present invention.
Figure 3B:
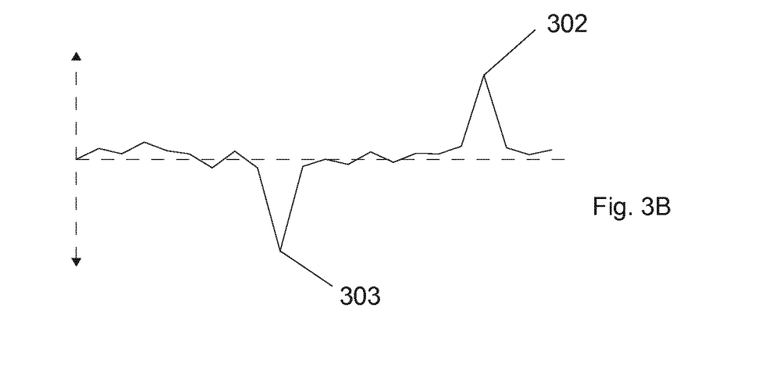
Figure 3C:
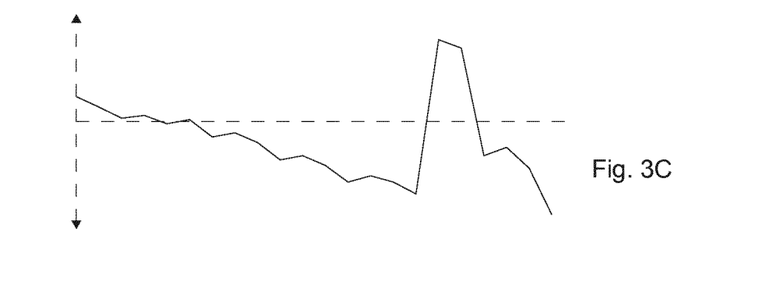

FIG. 3 illustrates different operating conditions as measured by any aggregate of sensor data, such as by a single sensor interface, for example a wear debris particle sensor interface, and the different patterns shown in FIGS. 3A through 3C illustrate the increased sensor sensitivity useful according to the present invention.

Firstly, all three sensor data sets average substantially around a mean value (301) and may be lost to conventional sensors. However, with the present invention, variance readings and accompanying higher signal fidelity allows reading the situations accurately.

FIG. 3A illustrates a mostly steady operating pattern with small variations in sensor input. By signaling the mean value and a variance based on this data, any subsequent changes to the sensor data is easier to interpret. Over time, the variance will for example steadily increase due to system wear. In one embodiment of the invention, this gradual change is compared with expected wear, and machine life is projected accurately. Deviations from this expected norm can be assessed, and improvements made to operations. In an embodiment of the invention, normal operation is monitored for a specified period of time, such as a month.

FIG. 3B illustrates a situation monitored much like the one seen in FIG. 3A, but with significant deviations, 302 and 303. With a variance as established in 3A, the probability of these deviations can be quantified, and the situation be understood better. In an embodiment of the invention, the readings leading up to a deviation hold information allowing an early alert, mitigating it or perhaps avoiding it entirely.

FIG. 3C illustrates a pattern of steadily declining readings with a sudden spike. Such a reading could be created by gradual clogging of a pipe, whereby wear debris particles gather at a point followed by a sudden release of these particles or by another event.

The increased fidelity and variance readings not only allow quantitatively better readings being closer to the actual situation in the system, but in turn also allow for more sophisticated pattern recognition, such as recognising a pattern as seen in FIG. 3C, where a sensor, which normalises data, would perhaps inaccurately produce a wavelike or sinusoidal curve from the same data set.

FIG. 4 illustrates individual sensor interface signals compounded into spiderweb form 400, a combination of values along these axes defining specific status patterns 401, 402 403. In the embodiment illustrated, small particles 411, large particles 412, water content 413, chemical composition 414 and temperature 415 are monitored. In other embodiments of the invention, other types of input can be used, such as pressure, and other combinations can be used, such as having more than one small particle sensor, either in different locations in the system or in the same location. As little as two sensors may be used or as many as convenient, the spiderweb accommodating this by fitting the number of axes used.

Figure 4A:
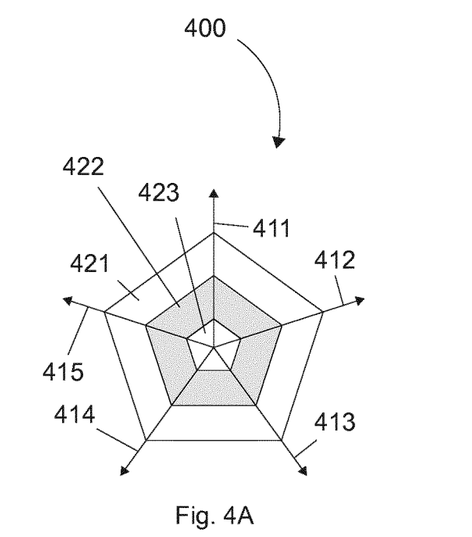
FIG. 4 illustrates example measurement data arranged in a spiderweb diagram for three operating states according to the present invention.

In FIG. 4A, the middle greyed out area 422 represents measurements within expected means, while the inner region 423 represents measurements lower than the expected, and the outer region 421 represents readings greater than the expected. This allows easy assessment of individual input.

Figure 4B:
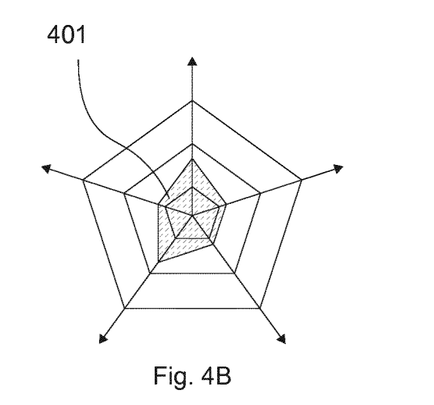

FIG. 4B illustrates a situation, where all signals are within the norm thus letting the maintenance crew know that the system is functioning. This, however, tells nothing about the pattern trajectory for which real-time changes must be taken into account which we will discuss below.

Figure 4C:
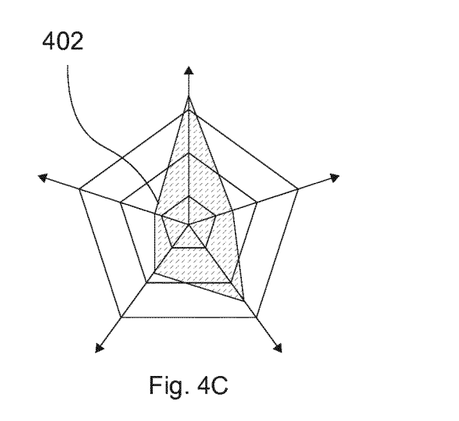

FIG. 4C illustrates the previously mentioned status pattern, where small particle count is extremely high, water content is high 402, and the rest of the sensor signals are within normalcy thresholds which constitutes an example situation, where perhaps no intervention is needed despite individual sensors signaling the need for a system stop.

Figure 4D:
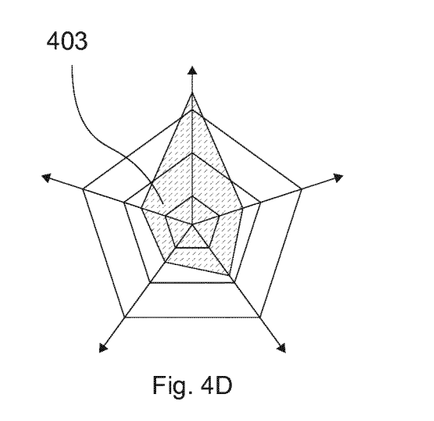

FIG. 4D, illustrates a status pattern much like the one described for FIG. 4C with extremely high small particle count and the rest of the measurement values being within normalcy thresholds 403, the difference being the water content being lower. Looking at sensor interface data individually, this seems perhaps more benign than the aforementioned pattern 402, while in fact this situation likely requires a system stop and an intervention.

These patterns 402, 403 are merely example patterns excelling in their communicability. The present invention allows identification of patterns specific to individual systems as well as identifying nuanced and contextual intervention needs in general for a given system and in an embodiment of the invention, a method according to the invention is likely to produce a much longer list of patterns than could usefully be described here.

Figure 5:
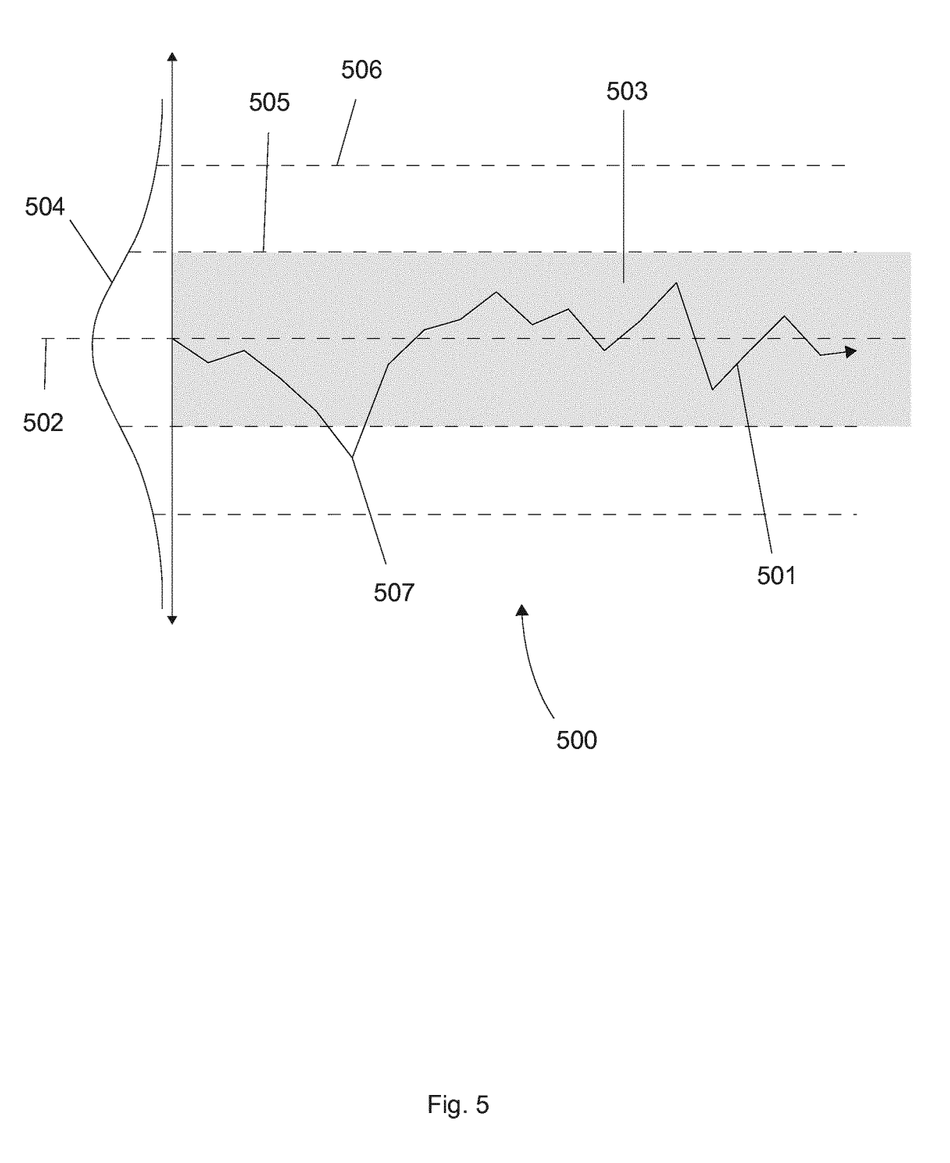
FIG. 5 illustrates a control function according to the present invention.

FIG. 5 illustrates a real-time operating graph 500 comprising a compounded multivariable control function 501 developed based on the status patterns, such as those previously discussed 401, 402, 403. The operating pattern operates around an aggregated operations mean value 502 with an aggregated operations variance 503.

In the illustrated embodiment, the combined variance defines the safe operating space although this view of safe operation is simplified. In another embodiment, safe operating space is smaller for some variables and larger for others depending on their system tendencies and causalities regardless of their tendency to achieve those values. For example, certain measurements may be acted on even within their variance if this is needed to maintain adequate system stability, while other measurement combinations may be allowed to transgress variance thresholds with no significant effect in the system. In the embodiment illustrated, the operating pattern is mostly maintained within the acceptable thresholds, while at one drop 507, it transgresses into a given undesirable state.

By assessing the likelihood and threat of combinations of sensor signals, where certain combinations are more likely and/or more disadvantageous than others, a combined mean and variance is developed with a high fidelity sensitivity to individual measurement deviations, when these deviations are historically known to be adverse to system performance or to promote such an effect.

Then, this compounded multivariable control function 501 operates according to a normal distribution and is expected to gravitate around a mean. A first deviation 505 and a second deviation 506 show the typical operating space for the operating pattern.

FIG. 6 illustrates data handling according to the present invention. During an initial operational phase 601, operational measurement data 610 is gathered through system monitoring through available sensor interfaces. In broad terms, this data handling comprises establishing an operational baseline for all parameters and comparing these with current readings. Optionally, it includes comparing operations with other, similar systems, and optionally, it includes re-establishing the baseline continually.

This initial operational phase 601 is performed after initial system run-in and preferably immediately after, but may also usefully be performed at any time during the lifetime of the system if for example the invention is fitted onto an existing system. The initial operational phase may have any duration, such as a day, a week, a month or a year. In one embodiment of the invention, the initial operational phase has a duration of one month. The aim of this phase is to map out expected system behavior through baseline data 610.

Using gathered baseline data 610, correlations are performed 602 on parameters comprising mutual relationships among parameters as well as optionally, relationships with system performance producing the operational map 611. Correlations comprise at least one-way relationships among all parameters, typically two-way relationships. Optionally, more complex relationships, such as for example conditional three-way relationships, may be included. For example, the state of a first parameter and a second parameter may affect a third parameter which was not affected by either the first or second parameter in isolation.

Also, these correlations may take any form. In one embodiment, the current state of one parameter corresponds to expected current sensor readings and/or variances for each other parameter. In another embodiment, correlations correspond to an expected change to a sensor reading or in other words, a trajectory. These relationships may even be more complicated, such as a combination of expected current sensor readings and/or variances and trajectories. For example, the relationship between wear debris particles and pressure may be a positive, reinforcing relationship, where an increase in one produces an increase in the other until a certain point, where a sudden pressure drop occurs signaling perhaps a fractured pipe.

The correlation may be a directed relationship or an undirected relationship. In an undirected relationship, the correlation is merely knowing that two parameters tend to take certain values together. A directed relationship is, where a change to a first parameter has a known effect on a second parameter, and a change to the second parameter has a known and perhaps different effect on the first parameter. Both or either of these directed relationships between two parameters may comprise one parameter having no effect on another parameter. Such a relationship may for example be the relationship between wear debris particle generation and liquid degradation. Liquid degradation may have a very significant effect on wear particle generation on eroding the machine parts, while wear debris particles may not degrade the liquid or may degrade the liquid at a different rate.

The operational map 611 combines parameters with each other and overall liquid condition to assess any given snapshot set of measurements to an expected system condition as well as optionally a pattern trajectory of expected future operating conditions comparing the current state with similar past states. Also, the operational map optionally contains the mean values and variances of individual sensor interface measurements and/or an aggregated sensor interface measurement.

A second operational phase 603 is then initiated, where the operational map 611 is utilised to evaluate the state and trajectory of the control function 501 to perform pattern predictions 604. For example, these pattern predictions recognises the aforementioned example of ignoring high particle count if water content is high, and this has previously been found to be benign.

In one embodiment of the invention, data gathered throughout the second operational phase 603 is used as updated baseline data 610 or in other words, used to evaluate a drift to the parameters determined based on the previously collected baseline data. This allows calibrating the operational map 611 as operational conditions change, such as due to wear.

In one embodiment of the invention, baseline data 610 and/or the operational map 611 is communicated to a convenient location, where inter-system data 620 is stored. This allows modelling likely operation patterns across systems and comparing operational maps and the change to these over time. In one embodiment of the invention, correlations 602 consider inter-system data 620, allowing that new systems fitted with the present invention have increased precision and expected wear patterns developed through previous installments.

The invention claimed is:

1. A sensing unit for monitoring a condition of a liquid, said sensing unit comprising:
at least one sensor interface, said at least one sensor interface configured to measure two or more unfiltered raw signals, the unfiltered raw signals corresponding to at least two different physical parameters of a liquid, wherein each of the physical parameters comprises at least one of: (a) a degradation of the liquid, (b) a presence of wear debris particles in the liquid, (c) a particle content of the liquid, (d) a particle count of the liquid, or (e) a viscosity of the liquid, wherein the each one of the unfiltered raw signals provides a mean value and a non-zero variance over a course of at least two measurements, the at least one sensor interface further configured to transmit said unfiltered raw signals as unfiltered transmission signals, each of the unfiltered transmission signals being based on one of the unfiltered raw signals and having a variance equal to the non-zero variance of one of the unfiltered raw signals; and
an evaluation unit operatively coupled to the at least one sensor interface,
wherein, as a result of receiving the unfiltered transmission signals, the evaluation unit is configured to evaluate a condition of the liquid based on a relationship between the at least two different physical parameters.

2. The sensing unit of claim 1, wherein:
a first portion of the liquid is located between a reservoir outlet and a filter inlet; and
a second portion of the liquid is located between a filter outlet and a reservoir inlet, wherein the at least one sensor interface is configured to measure the unfiltered raw signals based on sensing at least one of (a) the first portion of the liquid; or (b) the second portion of the liquid.

3. The sensing unit of claim 1, wherein:
the at least one sensor interface comprises a first sensor interface:
the sensing unit comprises a second sensor interface configured to measure the unfiltered raw signals; and
the evaluation unit is operatively coupled to the second sensor interface.

4. The sensing unit of claim 3, wherein:
a first portion of the liquid is located between a reservoir outlet and a filter inlet;
a second portion of the liquid is located between a filter outlet and reservoir inlet;
the first sensor interface is configured to measure the unfiltered raw signals based on sensing the first portion of the liquid; and
the second sensor interface is configured to measure the unfiltered raw signals based on sensing the second portion of the liquid.

5. The sensing unit of claim 1, wherein the at least one sensor interface is configured to measure the unfiltered raw signals based on sensing at least one of: (a) a first portion of the liquid located upstream of a filter; or (b) a second portion of the liquid located downstream of the filter.

6. A system for monitoring a condition of a liquid, the system comprising:
a system inlet configured to receive contaminated liquid;
a system outlet configured to receive filtered liquid;
a filtration unit in fluid communication with the system inlet and the system outlet, the filtration unit comprising a filter which is configured to receive the contaminated liquid and to release the filtered liquid; and
a sensor unit comprising:
at least one sensor interface configured to:
fluidly interface with at least one of: (a) the contaminated liquid flowing toward the filter; or (b) the filtered liquid flowing away from the filter; and
measure two or more unfiltered raw signals corresponding to at least two different physical parameters of at least one of the contaminated liquid or the filtered liquid, wherein each of the physical parameters comprises at least one of: (a) a liquid degradation, (b) a presence of wear debris particles, (c) a particle content, (d) a particle count, or (e) a viscosity, wherein the each one of the unfiltered raw signals is associated with a mean value and a non-zero variance derived over a course of at least two measurements, the at least one sensor interface further configured to transmit said unfiltered raw signals as unfiltered transmission signals, each of the unfiltered transmission signals being derived from one of the unfiltered raw signals and having a variance equal to the non-zero variance of one of the unfiltered raw signals; and
an evaluation unit operatively coupled to the at least one sensor unit, wherein:
the evaluation unit is configured to evaluate a condition of at least one of the contaminated liquid or the filtered liquid depending on a relationship between the at least two different physical parameters; and the evaluation is based, at least in part, on the unfiltered transmission signals received from the at least one sensor unit.

7. The system of claim 6, wherein the at least one sensor interface is configured to measure the unfiltered transmission signals based on sensing the filtered liquid that is located downstream of the filter and flowing away from the filter.

8. The system of claim 6, wherein the at least one sensor interface is configured to measure the unfiltered transmission signals based on sensing the contaminated liquid that is located upstream of the filter and flowing toward the filter.

9. The system of claim 6, wherein:
the liquid comprises the contaminated liquid and the filtered liquid;
the liquid comprises an oil product; and
the filter comprises an oil filter.

10. The system of claim 9, wherein a viscosity of the oil product is between 1 to 5,000 cSt.

11. The system of claim 9, wherein an operating temperature of the oil product is between 0 to 120° C.

12. A method of monitoring a condition of a liquid, the method comprising:
providing a sensing unit for monitoring the condition of the liquid, the sensing unit comprising at least one sensor interface;
measuring two or more different physical parameters of the liquid by use of the at least one sensor interface, wherein each of the physical parameters relates to at least one of: (a) a degradation of the liquid, (b) a presence of wear debris particles in the liquid, (c) a particle content of the liquid, (d) a particle count of the liquid; or (e) a viscosity of the liquid, wherein the at least one sensor interface provides at least two non-preprocessed raw signals corresponding to said two or more physical parameters and a mean value and a non-zero variance different from zero for each signal, the at least one sensor interface being operable to transmit the at least two non-preprocessed raw signals to an evaluation unit, the signals being at least substantially non-aggregated during a time between when the signals are being provided by the at least one sensor interface and when the signals are being transmitted to the evaluation unit; and
providing an evaluation unit that is operable to receive the at least two non-preprocessed raw signals and evaluate a condition of the liquid based on a relationship between the two or more different plurality of the physical parameters.

13. The method of claim 12, wherein said two or more physical parameters are included in an operational map comprising a plurality of correlations against each one of the physical parameters, the operational map configured to be modified to accommodate shifts in parameter mean values and variances over time.

14. The method of claim 12, further comprising comparing the two or more physical parameters to a set of intersystem data, the intersystem data being data from previously operated comparable systems for monitoring the condition of a liquid.

15. The method of claim 12, wherein the evaluation of the two or more physical parameters of the liquid is carried out continuously.

16. The method of claim 12, wherein the evaluation unit is configured to emit a signal indicating the evaluated condition of the liquid.

17. The method of claim 12, wherein:
a first portion of the liquid is located between a reservoir outlet and a filter inlet; and
a second portion of the liquid is located between a filter outlet and a reservoir inlet, wherein the at least one sensor interface is configured to measure the non-preprocessed raw signals based on sensing at least one of: (a) the first portion of the liquid; or (b) the second portion of the liquid.

18. The method of claim 12, wherein:
the at least one sensor interface comprises a first sensor interface;
the sensing unit comprises a second sensor interface configured to measure the non-preprocessed raw signals; and
the evaluation unit is operatively coupled to the second sensor interface.

19. The method of claim 18, wherein:
a first portion of the liquid is located between a reservoir outlet and a filter inlet;
a second portion of the liquid is located between a filter outlet and a reservoir inlet;
the first sensor interface is configured to measure the non-preprocessed raw signals based on sensing the first portion of the liquid; and
the second sensor interface is configured to measure the non-preprocessed raw signals based on sensing the second portion of the liquid.

20. The method of claim 12, wherein the at least one sensor interface is configured to measure the non-preprocessed raw signals based on sensing at least one of: (a) a first portion of the liquid located upstream of a filter; or (b) a second portion of the liquid located downstream of the filter.

* * * * *